United States Patent
Kolodziej et al.

(10) Patent No.: US 7,776,316 B2
(45) Date of Patent: Aug. 17, 2010

(54) COSMETIC COMPOSITION CONTAINING A PHOTOCHROMIC COLOURING AGENT AND ITS USE FOR SKIN AND/OR SKIN APPENDAGE MAKE-UP AND/OR CARE

(75) Inventors: Richard Kolodziej, Paris (FR); Nicolas Soistier, Boulogne (FR); Jean-Christophe Simon, Paris (FR)

(73) Assignee: L'Oreal, Paris (FR)

( * ) Notice: Subject to any disclaimer, the term of this patent is extended or adjusted under 35 U.S.C. 154(b) by 810 days.

(21) Appl. No.: 10/168,537

(22) PCT Filed: Oct. 30, 2001

(86) PCT No.: PCT/FR01/03370

§ 371 (c)(1),
(2), (4) Date: Oct. 28, 2002

(87) PCT Pub. No.: WO02/36083

PCT Pub. Date: May 10, 2002

(65) Prior Publication Data

US 2003/0118531 A1 Jun. 26, 2003

(30) Foreign Application Priority Data

Oct. 31, 2000 (FR) .................................. 00 14027

(51) Int. Cl.
*A61Q 1/02* (2006.01)
(52) U.S. Cl. ........................... 424/63; 424/401; 424/61; 424/64; 424/69; 424/70.1; 252/586; 252/588
(58) Field of Classification Search .................. 424/63, 424/401
See application file for complete search history.

(56) References Cited

U.S. PATENT DOCUMENTS

| 3,058,931 | A | * | 10/1962 | Petty .......................... 523/171 |
| 5,066,485 | A | * | 11/1991 | Brieva et al. ................... 424/63 |
| 5,176,905 | A | | 1/1993 | Ohno et al. |
| 5,628,934 | A | | 5/1997 | Ohno et al. |
| 5,762,915 | A | | 6/1998 | Saito et al. |
| 5,827,508 | A | * | 10/1998 | Tanner et al. .................. 424/59 |
| 6,190,677 | B1 | * | 2/2001 | Remy .......................... 424/401 |
| 6,468,550 | B1 | * | 10/2002 | Remy .......................... 424/401 |
| 2003/0017123 | A1 | * | 1/2003 | Scancarella et al. ........... 424/63 |

FOREIGN PATENT DOCUMENTS

| EP | 0 998 901 | | 5/2000 |
| EP | 0998 901 A1 | * | 5/2000 |
| EP | 0998901 | * | 5/2000 |

OTHER PUBLICATIONS

Sagrin, dward, Cosmetics, Science and Technology, 1966, Color in Cosmetics, Chapter 44, Samuel Zuckerman, pp. 1075-1101.*
Sagrin, Edward, Cosmetics, Science and Technology, 1966, Color in Cosmetics, Chapter 44, Samuel Zuckerman, pp. 1075-1102.*

* cited by examiner

*Primary Examiner*—Robert A Wax
*Assistant Examiner*—Bethany Barham
(74) *Attorney, Agent, or Firm*—Oblon, Spivak, McClelland, Maier & Neustadt, L.L.P.

(57) ABSTRACT

Liquid cosmetic composition in the form of an emulsion comprising at least two distinct phases and containing at least one photochromic coloring agent and at least one non-photochromic coloring matter, characterized in that the photochromic coloring agent(s) and the non-photochromic coloring matter(s) are located in separate phases of the emulsion.

Application to the make-up and/or the care of the skin and/or its appendages.

32 Claims, No Drawings

COSMETIC COMPOSITION CONTAINING A PHOTOCHROMIC COLOURING AGENT AND ITS USE FOR SKIN AND/OR SKIN APPENDAGE MAKE-UP AND/OR CARE

The present invention relates to an emulsified liquid composition for care and/or treatment and/or make-up of the skin and/or its appendages containing at least two distinct phases, one comprising photochromic colouring agents and the other comprising non-photochromic colouring matters to improve the photochromic properties of the photochromic colouring agent.

The known compositions used in make-up are constituted of a suitable vehicle and various colouring agents designed to confer a certain colour to the compositions, before and/or after their application to the skin.

The range of colouring agents presently used by cosmeticians is quite limited. These agents are mainly organic pigments, lacquers, pearlescent or mineral pigments.

The lacquers make it possible to obtain bright colours but most of them are unstable to light, temperature and pH. Some also have the disadvantage of staining the skin in an unsightly manner after application by discharge of the colouring matter.

The mineral pigments, in particular the mineral oxides, are on the other hand very stable but give rather lacklustre and pale colours.

The pearlescent pigments make it possible to obtain varied colours but which are not intense, with most often quite weak iridescent effects.

It has thus been proposed to use photochromic colouring agents in make-up or hair compositions so as to obtain pleasant and variable changes in the "colour return" of the make-ups for the skin and/or the hair.

A photochromic colouring agent is an agent having the property of changing colour and/or opacity when it is illuminated by ultraviolet light in the presence or absence of visible light, and of returning to the initial state when it is no longer illuminated by ultraviolet light. By colour is meant any colour of the visible spectrum.

Such colouring agents find a particularly attractive application in cosmetic compositions, in particular in the make-up compositions such as foundation creams, rouges or eyelid make-up, mascaras, eye-liners, lipsticks, shimmer sticks and nail polishes.

In fact, it has been observed that the "make-up return" of a made-up skin with such a composition is different depending on whether one is in natural or artificial light. Thus, a make-up applied in artificial light will appear lighter in natural light. Conversely, make-up applied outdoors will appear darker under artificial illumination. The make-up takes on a colour adapted to the environment of the consumer.

The combined use of photochromic colouring agents and non-photochromic colouring matters in cosmetic compositions is well-known. In these known applications, the photochromic colouring agents and non-photochromic colouring matters are contained in the same phase.

Thus, the European patent EP-359,909 describes an emulsified foundation cream containing a photochromic pigment and a non-photochromic conventional pigment. It seems clear, if reference is made to the mode of preparation, that the photochromic pigment and the non-photochromic pigment are contained in one and the same phase.

Moreover, the European patent application EP-898,952 describes the use of an ionic conductor to improve the photochromism of a composition, in particular a cosmetic composition, containing a photochromic compound and optionally non-photochromic colouring matters usually used in the cosmetic compositions, such as pigments, pearlescent preparations, fillers or organic colorants.

Similarly, U.S. Pat. No. 5,989,573 proposes the use of a particular constituent to improve the photochromism of a cosmetic composition containing a photochromic compound and optionally non-photochromic colouring matters, the particular constituent being likely to occupy at least one vacant state of an energy band corresponding to an empty electronic shell of the photochromic compound.

Now it has been observed that when photochromic colouring agents and non-photochromic colouring matters are combined, these latter impair the photochromic properties of the photochromic colouring agents.

The purpose of the invention is hence to provide a cosmetic composition, in particular for the care and/or treatment and/or make-up of the skin and/or its appendages, in particular of the face and human body such as the lips, the hair, the eyelashes, the eyebrows and nails, comprising both photochromic colouring agents and non-photochromic colouring matters, which possesses improved photochromic properties.

The purpose of the invention is also the use of a composition such as previously defined to care for and/or make-up and/or protect the skin and/or its appendages of the face and human body.

The purpose of the invention is also the use of a composition such as previously defined to prepare an ointment designed to treat and/or protect the skin and/or its appendages of the face or human body.

The photochromic properties of a compound may be characterized with the aid of the trichromatic co-ordinates (L, a and b) in the manner described in the Examples. These co-ordinates make possible in particular the determination of the parameter $\Delta E_{15}$ which will serve, in the present application, to characterize the photochromism of the photochromic colouring agents. Generally speaking, the higher the parameter $\Delta E15$, the more the compound is likely to change colour after irradiation.

Thus, the purpose of the invention is to improve the parameter $\Delta E_{15}$ of the composition, i.e. to obtain the highest possible value for the parameter $\Delta E_{15}$.

More precisely, the objectives of the present invention are attained by producing a liquid cosmetic composition in the form of an emulsion comprising at least two distinct phases and containing at least one photochromic colouring agent and at least one non-photochromic colouring matter, characterized in that the photochromic colouring agent(s) and the non-photochromic colouring matter(s) are found in separate phases of the emulsion.

The photochromic colouring agents and the non-photochromic colouring matters are either dissolved or dispersed, depending on their solubility. The photochromic colouring agents are usually dissolved if they are soluble and the non-photochromic pigments are dispersed.

The photochromic colouring agent may be selected from all of the photochromic compounds of the prior art capable of being used in the field of application under consideration.

In particular, mention may be made of the complex, mineral photochromic compounds and more particularly the doped aluminosilicates and the metal oxides and oxide hydrates.

The aluminosilicates have a basic structure that consists of a cage formed by tetrahedra of $AlO_4$ and $SiO_4$, linked together by their oxygen atoms. Some chemical elements may be present in the cages thus formed. These elements are called "doping elements". The doped aluminium silicate is hence an aluminium silicate that contains at least one doping element. These doping elements may be halogen anions such as the chloride, iodide, bromide or fluoride anions, alone or in a mixture. The doping elements may also be present in the form of sulfur, selenium, $SO_4^{2-}$, $WO_4^{2-}$ or hydroxyl groups, or also in the form of metal ions such as ions obtained from iron, chromium, manganese, cobalt and/or nickel. It is also possible to use a mixture of these different doping elements.

Of the doped aluminium silicates, mention may be made of those described in the application EP-A-0,847,751. These compounds preferably have a structure of the type: $R_8Al_6Si_6O_{24}X_n$ in which:
R represents an element selected from the elements Na, K, Cs, Rb, Li, Ag or Ca, and preferably R represents Na; and
X represents one or more doping elements such as defined above,
n varies from 1 to 5, and preferably from 1 to 3.

Of these compounds particular mention may be made of the family of the sodalites which have the formula: $Na_8Al_6Si_6O_{24}X_2$, in which $X_2$ represents one or more halogen anions and in particular $Cl_2$, ClBr, $I_2$ or $Br_2$.

Mention may also be made of the mineral photochromic compounds selected from the metal oxides, hydrates of said oxides and their complexes such as those described in the patents U.S. Pat. No. 5,989,573 and EP-B1-0,359,909 and in particular the oxides of titanium, niobium, silicon, aluminium, zinc, hafnium, thorium, tin, thallium, zirconium, beryllium, cobalt, calcium, magnesium, iron and their mixtures. Of these metal oxides, particular mention may be made of the oxides of titanium, aluminium, zinc, zirconium, calcium, magnesium, silicon and iron. The oxides and oxide hydrates of titanium, aluminium, zinc, zirconium, calcium and magnesium are preferred. Even more preferably use should be made of titanium dioxide which can be made photochromic with the aid of a metal selected from iron, chromium, copper, nickel, manganese, cobalt, molybdenum as such or in the form of a salt such as a sulfate, chlorate, nitrate, acetate.

The photochromic colouring agent may be incorporated in the cosmetic composition according to the invention in a quantity that can easily be determined by the specialist skilled in the art on the basis of his general knowledge, and which may represent from 0.01 to 30% by weight of the total weight of the composition, and preferably from 1 to 16% by weight.

The cosmetic composition according to the invention also contains non-photochromic colouring matters, selected from the colouring matters usually used in cosmetic compositions, in particular pigments, fillers, pearlescent preparations, lipophilic colorants, hydrophilic colorants and their mixtures.

By pigments is meant white or coloured particles, mineral or organic, insoluble in the hydrophilic liquid phase, designed to colour the composition and/or render it opaque. Most often, such pigments are of one colour.

By fillers is meant colourless or white particles, mineral or synthetic, lamellar or non-lamellar, designed to give body and rigidity to the composition, and/or softness, dullness and uniformity to the make-up.

By pearlescent preparations is meant iridescent particles, in particular produced by certain molluscs in their shell or synthetic. These fillers and pearlescent preparations serve in particular to modify the texture of the composition.

The pigments may be white or coloured, mineral and/or organic, of usual size or nanometric or goniochromatic.

As mineral pigments that can be used according to the invention mention may be made of the oxides of titanium, zirconium or cerium as well as oxides of zinc, iron or chromium, ferric blue, chromium hydrate and their mixtures. Of the organic pigments which can be used according to the invention mention may be made of carbon black, the ultramarines (aluminosilicate polysulfides), manganese pyrophosphate and certain metal powders such as those of silver or aluminium, lacquers of barium, strontium, zirconium, calcium, aluminium, diketopyrrolopyrrole (DDP) described in the documents EP-A-542,689, EP-A-787,730, EP-A-787, 731 and WO 96/08537, and their mixtures.

As interferential goniochromatic pigments mention may be made of the liquid crystal (LC) type pigments like HELICONE® from WACKER described in the documents EP-A-0,815,826 and EP-A-0,953,33 or of the multilayer type (ML), like SICOPEARL FANTASTICO® from BASF described in the document EP-A-0,953,33.

The pigments may be present in the composition to the extent of 0 to 5%, and preferably from 0.01 to 5% by weight of the total weight of the composition.

The fillers that can be used according to the present invention may be selected from the group consisting of talc, zinc stearate, mica, silica, kaolin, Nylon powders (Orgasol in particular) and polyethylene, Teflon®, starch, boron nitride, microspheres of copolymers such as Expancel® (Nobel industry), Polytrap® (Dow Corning), polymethylmethacrylate microspheres, microbeads of silicon resin (Tospearl® of Toshiba, for example), precipitated calcium carbonate, magnesium carbonate or hydrocarbonate, metal soaps derived from organic carboxylic acids with 8 to 22 carbon atoms. The fillers may be present in a proportion of 0 to 30%, and preferably from 0.5 to 15% by weight of the total weight of the composition.

Of the pearlescent preparations that may be considered mention may be made of natural mother-of-pearl, mica coated with titanium oxide, iron oxide, natural pigment or bismuth oxychloride such as coloured titanium mica and their mixtures. The pearlescent preparations may be present in the composition in a proportion of 0 to 20%, and preferably from 0.01 to 15% by weight of the total weight of the composition.

The cosmetic composition according to the invention may in addition contain a colorant, in particular a natural organic colorant such as cochineal carmine and/or synthetic colorants such as the halogen acids, azo compounds and anthraquinones. Mention may also be made of mineral colorants such as copper sulfate.

The composition according to the invention is available in the form of an emulsion, in particular an oil-in-water emulsion (O/W), water-in-oil emulsion (W/O), or multiple, for example triple, emulsion. Preferably, it is available in the form of an oil-in-water (O/W) or water-in-oil (W/O) emulsion.

Generally, at least one of the phases is a fatty phase containing at least one organic solvent and the other phase is an aqueous phase.

According to a first embodiment of the invention, the photochromic colouring agent is found in the fatty phase and the non-photochromic colouring matter is found in the aqueous phase.

According to a second embodiment of the invention, the non-photochromic colouring matter is found in the fatty phase and the photochromic colouring agent is found in the aqueous phase.

The aqueous phase may contain water, a floral water such as cornflower and/or a mineral water such as Vittel water, Vichy waters, Uriage water, Roche Posay water, Bourboule water, Enghien-les-Sains water, Saint Gervais-les-Bains water, Allevar-les-Bains water, Digne water, Lucas water, Maizieres water, Neyrac-les-Bains water, Lons-le-Saunier water, the Eaux Bonnes, Rocherfort water, Saint Christau water, Fumades water and Tercis-les-Bains water.

Said aqueous phase may also contain from 0% to 25%, and preferably from 0.1 to 20% by weight of the total weight of the aqueous phase of a $C_2$-$C_8$ lower alcohol and/or a polyol such as glycerol, butylene glycol, isoprene glycol, propylene glycol, polyethylene glycol.

The fatty phase contains one or more cosmetically acceptable organic solvents (acceptable tolerance, toxicology and feel). These organic solvents may represent from 0% to 95%, and preferably from 0.1 to 90% by weight of the total weight of the fatty phase, and may be selected from the group constituted by the hydrophilic organic solvents, the lipophilic organic solvents, the amphiphilic solvents or their mixtures.

Of the hydrophilic organic solvents mention may be made for example of the linear and branched lower monoalcohols with from 1 to 8 carbon atoms like ethanol, propanol, butanol, isopropanol, isobutanol; the polyethylene glycols having from 6 to 80 ethylene oxides; the polyols such propylene glycol, isoprene glycol, butylene glycol, glycerol, sorbitol; the mono- or dialkyl isosorbides, the alkyl groups of which have from 1 to 5 carbon atoms; the glycol ethers such as diethylene glycol monomethyl or monoethyl ether and the propylene glycol ethers such as dipropylene glycol methyl ether.

As amphiphilic organic solvents mention may be made of the polyols such as the derivatives of polypropylene glycol and a fatty acid, of polypropylene glycol and a fatty alcohol like PPG-23 oleyl ether and PPG-36 oleate.

The lipophilic organic solvents may be volatile or non-volatile.

As non-volatile lipophilic organic solvents mention may be made for example of the fatty esters such as diisopropyl adipate, dioctyl adipate, the alkyl benzoates, isopropyl myristate, isopropyl palmitate, butyl stearate, hexyl laurate, isononyl isononanoate, 2-ethyl hexyl palmitate, 2-hexyl decyl laurate, 2-octyl decyl palmitate, 2-octyl dodecyl myristate, di-(2-ethyl-hexyl) succinate, diistearyl malate, 2-octyl dodecyl lactate, glyceryl triisostearate, diglyceryl triisostearate.

As volatile lipophilic organic solvent mention may be made as examples of:

cyclic volatile silicones having from 3 to 8 silicon atoms and preferably from 4 to 6. Examples are cyclotetradimethylsiloxane, cyclopentadimethylsiloxane or cyclohexadimethylsiloxane.

cyclocopolymers of the dimethylsiloxane/methylalkylsiloxane type, such as SILICONE FZ 3109 sold by the UNION CARBIDE company, which is a dimethylsiloxane/methyloctylsiloxane cyclocopolymer;

linear volatile silicones having from 2 to 9 silicon atoms. Examples include hexamethyldisoloxane, hexylheptamethyltrisiloxane or octylheptamethyltrisoloxane.

Mention may also be made of the hydrocarbon volatile oils such as the isoparaffins and in particular isododecane; fluorinated oils like that sold under the trade name GALDEN® (MONTEFLUOS).

The fatty phase may also contain fatty bodies liquid at b 25° C. such as non-volatile silicone oils, oils of animal, vegetable or mineral origin or fluorinated or perfluorinated oils.

Of the non-volatile silicone oils mention may be made of:

polyalkyl ($C_1$-$C_{20}$) siloxanes, and in particular those with terminal trimethylsilyl groups, preferably those with a viscosity lower than 0.06 m2/s included in which mention may be made of the linear polydimethylsiloxanes and the alkylmethylpolysiloxanes such as cetyldimethicone (name CTFA), silicones modified by aliphatic and/or aromatic groups, optionally fluorinated, or by functional groups such as hydroxyl, thiol and/or amine groups, phenylated silicone oils, in particular those of the formula:

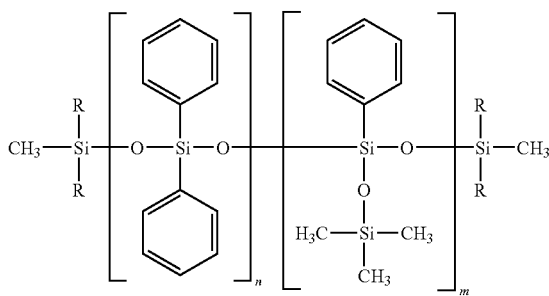

in which:

R is a $C_1$-$C_{30}$ alkyl radical, an aryl radical or an aralkyl radical, n is an integer from 0 to 100, and m is an integer from 0 to 100, provided that the sum (m+n) is an integer from 1 to 100.

Of the oils of animal, vegetable or mineral origin, and in particular the animal or vegetable oils consisting of esters of a fatty acid and polyols, in particular the liquid triglycerides, mention may be made of:

the oils of sunflower, maize, soya bean, squash, grape seed, sesame, hazelnut, apricot, almond or avocado; fish oils, glycerol tricaprocaprylate, animal or vegetable oils of the formula $R_1COOR_2$ in which $R_1$ represents the residue of a higher fatty acid comprising from 7 to 19 carbon atoms and $R_2$ represents a branched hydrocarbon chain containing from 3 to 20 carbon atoms, for example Purcelin oil; paraffin oil, vaseline oil, perhydrosqualene, wheat germ oil, calophyllum oil, sesame oil, macadamia oil, grape seed oil, rapeseed oil, coconut oil, peanut oil, palm oil, castor oil, jojoba oil, olive oil or cereal germ oil, the fatty acid esters; the alcohols; the acetylglycerides; the octanoates, decanoates or ricinoleates of alcohols or polyalcohols; the triglycerides of fatty acids; the glycerides.

The cosmetic composition according to the invention may also contain other fatty bodies which may be selected by the specialist skilled in the art on the basis of his general knowledge, so as to confer on the final composition the desired properties, for example of consistency and/or texture. These additional fatty bodies may be waxes, gums and/or viscous fatty bodies of animal, vegetable, mineral or synthetic origin, as well as their mixtures.

Particular mention may be made of:

silicone gums waxes of animal, vegetable, mineral or synthetic origin such as the microcrystalline waxes, paraffin, petrolatum, vaseline, ozocerite, montan wax; beeswax, lanolin and its derivatives; candelilla wax, Ouricury wax, carnauba wax, Japan wax, cocoa butter, cork fibre wax and cane sugar wax; hydrogenated oils solid at 25° C., the ozocerites, the fatty esters and glycerides solid at 25° C.; polyethylene waxes and waxes obtained by Fischer- Tropsch synthesis; hydrogenated oils solid at 25° C.; the lanolins; fatty esters solid at 25° C.; silicone waxes; fluorinated waxes.

The cosmetic composition according to the invention may also optionally contain at least one surfactant present in the composition in a proportion of 0 to 30%, and preferably from 0.1 to 25% by weight of the total weight of the composition.

These are principally anionic, non-ionic, amphoteric or zwitterionic derivatives.

It is possible to use one surfactant or a mixture of such surfactants.

Of the anionic surfactants that may be used alone or in a mixture mention may be made of the carboxylic acids and the salts of carboxylic acids. The carboxylic acids which may be used are fatty acids comprising a linear or branched alkyl chain, saturated or unsaturated, having from 6 to 16 carbon atoms and preferably from 10 to 14 carbon atoms. The salts of such fatty acids form soaps. As salts, it is possible to use for example alkali salts, alkaline earth salts, ammonium salts, the salts of aminoalcohols and the salts of amino acids, and in particular the sodium, potassium, magnesium, triethanolamine, N-methylglucamine, lysine and arginine salts. The carboxylic acid may be in particular lauric acid or myristic acid.

As soaps, mention may be made for example of the potassium salts of the $C_{10}$ to $C_{14}$ fatty acids, and in particular the potassium salt of lauric acid and the potassium salt of myristic acid.

As other anionic surfactants which can be used in the composition of the invention mention may be made for example of the othoxylated carboxylic acids and their salts; the sarcosinates and acyl-sarcosinates and their salts such as sodium lauroyl sarcosinate; the taurates and methyltaurates and their salts; the isethionates and acyl isethionates, reaction products of fatty acids comprising from 10 to 22 carbon atoms with isethionic acid, and their salts such as sodium isethionate and sodium cocoyl-isethionate; the sulfosuccinates and their salts, the alkylsulfates and alkylether sulfates and their salts, in particular sodium or triethanolamine laurylsulfate, and sodium or potassium laurylether sulfate; the phosphoric acid monoalkyl and dialkylesters and their salts, such as for example sodium mono- and dilauryl phosphate, potassium mono- and dilauryl phosphate, triethanolamine mono- and dilauryl phosphate, sodium mono- and dimyristyl phosphate, potassium mono- and dimyristyl phosphate, diethanolamine mono- and dimyristyl phosphate, triethanolamine mono- and dimyristyl phosphate; the alkane sulfonates and their salts; the bile salts such as the cholates, deoxycholates, taurocholates, taurodeoxycholates, the lipoamino acids and their salts such as the mono- and disodium acylglutamates; the bipolar, double surfactants such as described in Surfactant Sciences series, vol. 74 edited by Krister Homberg.

Of the non-ionic surfactants which can be used as surfactants mention may be made for example of the polyol ethers comprising fatty chains (8 to 30 carbon atoms) such as the fatty ethers of sorbitol or oxyethylene glycerols; the polyglycerol ethers and esters; the polyoxyethylene fatty alcohols which are for example ethers formed of ethylene oxide units and at least one fatty alcohol chain having from 10 to 22 carbon atoms. As examples of polyoxyethylene fatty alcohols mention may be made of the ethers of lauryl alcohol comprising more than 7 oxyethylene groups; the alkyl polyglucosides in which the alkyl group comprises from 1 to 30 carbon atoms, like for example decylglucoside, laurylglucoside, ketostearylglucoside, cocoyl glucoside; the akyl glucopyranosides and alkylthioglucopyranosides; the alkyl maltosides; the alkyl N-methylglucamides; the esters of polyoxyethylene sorbitan which usually contain from 1 to 100 ethylene glycol units and preferably from 2 to 40 ethylene oxide (EO) units; the esters of aminoalcohols and their mixtures.

As amphoteric or zwitterionic surfactants that can be used as surfactants mention may be made for example of the betaines such as dimethylbetaine, coco-betaine and coco-amidopropylbetaine; the sulfobetaines such as coco-amidopropylhydroxysultaine: the alkylamphoacetates such as cocoamphodiacetate; and their mixtures.

The composition according to the invention may also comprise from 0 to 10%, and preferably from 0.1 to 5% by weight of the total weight of the composition of at least one co-emulsifying agent which may be selected from the monostearate of oxyethylene sorbitan, fatty alcohols such as stearyl alcohol or cetyl alcohol or the eaters of fatty acids and polyols such as glyceryl stearate.

The composition according to the invention may also comprise one or more thickening agents in preferred concentrations ranging from 0 to 6%, and preferably from 0.1 to 5% by weight of the total weight of the composition. The thickening agent may be selected from:

polysaccharide biopolymers such as xanthan gum, carob gum, guar gum, the alginates, modified celluloses such as hydroxyethylcellulose, methylcellulose, hydroxypropylcellulose and carboxymethylcellulose, starch derivatives, cellulose ether derivatives possessing quaternary ammonium groups, cationic polysaccharides;

synthetic polymers such as the polyacrylic acids such as the glyceryl poly(meth) acrylate polymers such as HISPAGEL® or LUBRAGEL® from the HISPANO QUIMICA or GARDIAN companies, polyvinylpyrrolidone, polyvinyl alcohol, cross-linked polymers of acrylamide and ammonium acrylate such as PAS 5161 or BOZEPOL C® from HOECHST; acrylate/octylacrylamide copolymers such as Dermacryl® from National Starch; polyacrylamide-based polymers such as SEPIGEL® 305 from SEPPIC, cross-linked polymers of acrylamide and methacryloyloxyethyltrimethylmethylammonium chloride such as SALCARE® SC92 from ALLIED COLLOIDS, magnesium aluminium silicate.

The cosmetic composition according to the invention may or may not optionally comprise a film-forming polymer. These polymers may be dissolved or dispersed in the cosmetically acceptable medium. In particular, they may be present in the form of a solution in an organic solvent or in the form of a dispersion of polymer particles.

The compositions according to the invention advantageously comprise a stable dispersion of usually spherical particles of at least one polymer in a physiologically acceptable liquid phase. These dispersions may in particular be available in the form of nanoparticles of polymers as a stable dispersion in said fatty phase. The size of the nanoparticles is preferably comprised between 5 and 600 nm, given that above about 600 nm the dispersions become much less stable.

Yet another advantage of the polymer dispersion of the composition of the invention is the possibility of varying the transition temperature (Tg) of the polymer or polymer system (polymer plus additive of the plasticizer type) and of thus passing from a soft polymer to a more-or-less hard polymer, making it possible to control the mechanical properties of the composition as a function of the application envisaged.

It is possible to use polymers preferably having a low (Tg) or one equal to the temperature of the skin. A dispersion is thus obtained which can form a film when it is applied to a support, which is not the case when dispersions of mineral pigments according to the prior art used.

The usable polymers in the composition of the invention preferably have a molecular weight of the order of 2000 to 10,000,000 and a (Tg) of 100° C. to 300° C.

When the polymer exhibits too high a vitreous transition temperature for the use desired, it is possible to combine it with a plasticizer usually used in the field of application and in particular with the compounds likely to be solvents of the polymer.

Of the film-forming polymers mention may be made of radical homopolymers or copolymers, acrylic or vinyl, preferably having a Tg lower than 40° C. and in particular the methyl acrylates optionally copolymerized with acrylic acid and the cellulose derivatives such as nitrocellulose and cellulose acetobutyrate.

Of the non-film-forming polymers mention may be made of radical homopolymers or copolymers, vinyl or acrylic, optionally cross-linked, preferably having a Tg higher than or equal to 40° C. such as methyl polymethacrylate, polystyrene or tertiary butyl polyacrylate.

In a non-limiting manner, the polymers of the invention may be selected from the following polymers or copolymers: polyurethanes, acrylic polyurethanes, polyureas, polyurea-polyurethanes, polyester-polyurethanes, polyether-polyurethanes, polyesters, polyester-amides, polyesters with alkydes fatty chains: acrylic and/or vinyl polymers or copolymers: copolymers, acrylic-silicones: polyacrylamides: silicone polymers, fluorinated polymers and their mixtures.

Mention should be made in particular of the copolymers of (meth) acrylic acid and at least one linear, branched or cyclic (meth) acrylic acid ester monomer and/or at least one linear, branched or cyclic mono- or disubstituted (meth) acrylic acid amide monomer; the copolymers (meth) acrylic acid/tertiary butyl (meth) acrylate and/or isobutyl (meth) acrylate/($C_1$-$C_4$) alkyl (meth) acrylate; the terpolymers (meth) acrylic acid/ethyl acrylate/methyl methacrylate; the tetrapolymers methyl methacrylate/butyl or ethyl acrylate/hydroxyethyl or 2-hydroxypropyl methacrylate or acrylate/(meth) acrylic acid; the copolymers of acrylic acid and $C_1$-$C_4$ alkyl methacrylate; the terpolymers of vinyl pyrrolidone, acrylic acid and $C_1$-$C_{20}$ alkyl methacrylate, the amphoteric copolymers; the vinyl esters of branched acids; the vinyl esters of benzoic acid; the copolymers of (meth) acrylic acid and at least one olefinic monomer; the copolymers of a vinylic monoacid and/or an allylic monoacid.

Of the resins mention may be made of the resins of the aryl-sulfonamide formaldehyde or aryl sulfonamide epoxy type; the resins of the acrylic, styrene, acrylate-styrene and vinyl type, and the siliconized resins.

The composition according to the invention may also comprise at least one plasticizer, such as tricresyl phosphate, benzyl benzoate, triethyl citrate, tributyl citrate, triethyl acetylcitrate, 2-triethyl hexyl acetylcitrate, camphor; glycol ethers, castor oil oxyethylenated with 40 moles of ethylene oxide; propylene glycol; butyl glycol; ethylene glycol monomethyl ether acetate, propylene glycol ethers; ethers esters of propylene glycol and ethylene glycol; esters of diacids such as diethyl, dibutyl and diisopropyl phthalates and adipates, diethyl and dibutyl tartrates, diethyl and dibutyl succinates, diethyl and dibutyl sebacates, diethyl, dibutyl and 2-diethyl hexyl phosphates, diethyl and dibutyl acetyl citrate; glycerol esters. The plasticizers may usually be present in a content ranging from 1% to 40% by weight of the total weight of the composition.

The composition according to the invention may, in addition, comprise at least one of the ingredients conventionally used in the fields concerned and more especially in the cosmetic and dermatological fields. These ingredients are selected in particular from preservatives, aqueous or fatty phase thickeners (polysaccharide biopolymers, synthetic polymers), perfumes, hydrophilic active agents (hydrating agents for example selected from the group constituted by water or polyhydric alcohols having from 2 to 8 carbon atoms and from 2 to 6 hydroxyl functions, selected for example from ethylene glycol, glycerol, 1,2-propanediol, diglycerol, erythritol, arabitol, adonitol, sorbitol, dulcitol and D-panthenol) or lipophilic active agents (for example, selected from the group constituted by lanolin and the UVA or B filters), antioxidants, colorants, essential oils, plant extracts, vitamins and their derivatives (such as the vitamins A, B, C and E), the sphingolipids (ceramides), liposoluble polymers in particular the hydrocarbons (such as polybutene, the polyalkylenes, the polyacrylates and the siliconized polymers compatible with the body fats), and their mixtures.

The quantities of these different ingredients are those conventionally used in the fields concerned and, for example, range from 0 to 20%, and preferably from 0.01 to 15% by weight of the total weight of the composition.

Naturally, the specialist skilled in the art will take care to choose possible additional compounds and/or their quantity so that the advantageous properties of the cosmetic product according to the invention are not substantially or not at all impaired by the addition envisaged.

The composition according to the invention may be a product for the care and/or treatment and/or make-up of the skin. The compositions according to the invention find a particular application in the field of foundation creams and care creams, tinted or not.

Naturally, the composition according to the invention must be cosmetically acceptable, i.e. contain a physiologically acceptable medium, non-toxic and capable of being applied to the skin of human beings.

The invention is illustrated in more detail in the following Examples. In the Examples, unless indicated otherwise, all the percentages and parts are expressed by weight.

EXAMPLES

Method of Determination of the Parameter ΔE with the Aid of the Trichromatic Co-Ordinates The photochromic properties of a given compound (for example, the photochromic colouring agent) can be characterized in the following manner, with the aid of the trichromatic co-ordinates (L, a and b).

The powdered compound is packed into a metal cup.

The trichromatic co-ordinates ($L_0$, $a_0$, $b_0$) of the packed powder are measured with the aid of a colorimeter "CM 2002".

The cup is irradiated for 15 minutes with the aid of a lamp emitting over the whole of the solar spectrum (xenon lamp, Suntest CPS of Heraeus trademark, reproducing the solar spectrum), then the new coordinates ($L_{15}$, $a_{15}$ and $b_{15}$) are measured, which reflect the colour change on irradiation.

The parameter $\Delta E_{15}$ is determined in the following manner:

$$\Delta E_{15}=[(L_{15}-L_0)^2+(a_{15}-a_0)^2+(b_{15}-b_0)^2]^{1/2}$$

For all of the Examples, the photochromic colouring agent consists of titanium oxide and silica doped with iron, sold by the C.C.I.C. company through the intermediary of IKEDA under the trade name "PHOTOGENICA® 4".

In order that the comparisons made have their full significance, each foundation cream possesses, in identical proportions, the same non-photochromic mineral pigments and the same photochromic colouring agent ("PHOTOGENICA® 4").

Example 1

A first emulsified foundation cream FDT 1 according to the invention, by mixing the ingredients indicated in Table 1 as follows:

The photochromic colouring agent PHOTOGENICA® 4 is dissolved in a little water and propylene glycol at room temperature. All of the pigment slurry is then ground with the tricylinder device (3 passes).

The non-photochrome mineral pigments (yellow, red and black iron oxides) are dissolved in a little isononyl isononanoate at room temperature. All of the pigment slurry is then ground with the tricylinder device (3 passes).

The remainder of the water is introduced into a beaker M1 and heated to a temperature of 75° C. Stirring with the Raynerie stirrer (moderate) is started and the Veegum is added.

After waiting for 10 minutes the polysorbate 20 and the remainder of the propylene glycol are added.

The pigment slurry containing the photochromic colouring agent PHOTOGENICA® 4 is added to the beaker M1. Stirring and the temperature are maintained.

The filler is added.

The remainder of the isononyl isononanoate is heated to 75° C. in a beaker M2. The stearic acid and methyl glucose sesquistearate are added with stirring with the Raynerie stirrer.

After 15 minutes, the pigment slurry containing the non-photochromic mineral pigments (yellow, red and black iron oxides) are placed in the beaker M2.

When these pigments have been well dispersed, the emulsion is started by pouring the contents of beaker M2 into beaker M1, under vigorous stirring with a Moritz stirrer, for 10 minutes.

The rate of stirring is reduced and silicone is added. After waiting for 10 minutes, the water is added.

Example 2

A second foundation cream FDT 2 according to the invention, by mixing the ingredients indicated in Table 1 as follows:

The photochromic colouring agent PHOTOGENICA® 4 is dissolved in a little isononyl isononanoate at room temperature. All of the pigment slurry is then The non-photochrome mineral pigments (yellow, red and black iron oxides) are dissolved in a little water and propylene glycol at room temperature. All of the pigment slurry is then ground with the tricylinder device (3 passes).

The remainder of the water is introduced into a beaker M1 and heated to a temperature of 75° C. Stirring with the Raynerie stirrer (moderate) is started and the Veegum is added.

After waiting for 10 minutes the polysorbate 20 and the remainder of the propylene glycol are added.

The pigment slurry containing the non-photochromic mineral pigments is added to the beaker M1. Stirring and the temperature are maintained.

The filler is added.

The remainder of the isononyl isononanoate is heated to 75° C. in a beaker M2. The stearic acid and methyl glucose sesquistearate are added with stirring with the Raynerie stirrer.

After 15 minutes, the pigment slurry containing the photochromic colouring agent PHOTOGENICA® 4 is placed in the beaker M2.

When these pigments have been well dispersed, the emulsion is started by pouring the contents of beaker M2 into beaker M1, under vigorous stirring with a Moritz stirrer, for 10 minutes.

The rate of stirring is reduced and silicone is added. After waiting for 10 minutes, the water is added.

Comparative Example 3

A third foundation cream FDT 3 by mixing the ingredients indicated in Table 1 as follows:

The photochromic colouring agent PHOTOGENICA® 4 and the non-photochrome mineral pigments (yellow, red and black iron oxides) are dissolved in a little water and propylene glycol at room temperature. All of the pigment slurry is then ground with the tricylinder device (3 passes).

The remainder of the water is introduced into a beaker M1 and heated to a temperature of 75° C. Stirring with the Raynerie stirrer (moderate) is started and the Veegum is added.

After waiting for 10 minutes the polysorbate 20 and the remainder of the propylene glycol are added.

The pigment slurry containing the photochromic colouring agent PHOTOGENICA® 4 and the non-photochrome mineral pigments are added to the beaker M1. Stirring and the temperature are maintained.

The filler is added

The remainder of the isononyl isononanoate is heated to 75° C. in a beaker M2. The stearic acid and methyl glucose sosquistearate are added with stirring with the Raynerie stirrer.

After 15 minutes, the emulsion is started by pouring the contents of beaker M2 into beaker M1, under vigorous stirring with a Moritz stirrer, for 10 minutes.

The rate of stirring is reduced and silicone is added. After waiting for 10 minutes, the water is added.

TABLE 1

| Composition | FDT1 (%) | FDT2 (%) | FDT3 (%) |
| --- | --- | --- | --- |
| Water | 37.6 | 37.6 | 37.6 |
| Veegum | 0.7 | 0.7 | 0.7 |
| Propylene glycol | 6 | 6 | 6 |
| Polysorbate 20 | 3.7 | 3.7 | 3.7 |
| Yellow iron oxide | 0.22 | 0.22 | 0.22 |
| Red iron oxide | 0.12 | 0.12 | 0.12 |
| Black iron oxide | 0.05 | 0.05 | 0.05 |
| Photogenica 4 | 8.61 | 8.61 | 8.61 |
| Nylon | 4.5 | 4.5 | 4.5 |
| Isononyl Isononanoate | 21.7 | 21.7 | 21.7 |
| Stearic acid | 1 | 1 | 1 |
| Methyl glucose sesquistearate | 3.5 | 3.5 | 3.5 |
| Silicone | 10 | 10 | 10 |
| Water | 2.3 | 2.3 | 2.3 |

The characteristics of the mixtures are measured in accordance with the above method. The results given in Table 4 are obtained:

|     | $\Delta E_{15}$ |
| --- | --- |
| FDT1 | 5,6 |
| FDT2 | 5,6 |
| FDT3 | 5,03 |

Hence it is observed that for the same proportion of mineral pigments and photochromic colouring agent, the separation of these pigments makes it possible to obtain an appreciably higher value of the parameter $\Delta E_{15}$

The invention claimed is:

1. An emulsion comprising at least one photochromic coloring agent selected from the group consisting of titanium oxides, aluminum oxides, zinc oxides, zirconium oxides, calcium oxides, magnesium oxides, silicon oxides, iron oxides, and mixtures thereof, and at least one non-photochromic coloring matter selected from the group consisting of pigments, white fillers, pearlescent preparations, lipophilic colorants, hydrophilic colorants, and mixtures thereof, wherein the emulsion comprises at least two phases, wherein the photochromic coloring agent and the non-photochromic coloring matter are present in separate phases of the emulsion, and wherein the $\Delta E_{15}$ value of the emulsion is higher than the $\Delta E_{15}$ value of the same emulsion which differs only in that the photochromic coloring agent and the non-photochromic coloring matter are present in the same phase.

2. The emulsion according to claim 1, wherein the photochromic coloring agent is an oxide of titanium comprising iron, chromium, copper, nickel, manganese, cobalt, or molybdenum.

3. The emulsion according to claim 1, wherein the photochromic coloring agent is present in an amount of from 0.01 to 30% by weight of the total weight of the emulsion.

4. The emulsion according to claim 1, wherein the non-photochromic coloring matter is selected from the group consisting of lipophilic colorants, hydrophilic colorants, mineral pigments, organic pigments, pearlescent preparations and mixtures thereof.

5. The emulsion according to claim 4, wherein the non-photochromic coloring matter is a pigment present at a concentration of 0 to 5% by weight of the total weight of the emulsion.

6. The emulsion according to claim 4, wherein the non-photochromic coloring matter is a mineral pigment selected from the group consisting of yellow iron oxide, red iron oxide, black iron oxide and mixtures thereof.

7. The emulsion according to claim 1, wherein said emulsion is in the form of a water-in-oil (W/O) emulsion.

8. The emulsion according to claim 1, wherein said emulsion is in the form of an oil-in-water (O/W) emulsion.

9. The emulsion according to claim 1, wherein said emulsion is in the form of a multiple emulsion.

10. The emulsion according to claim 1, wherein at least one of the phases is a fatty phase comprising at least one organic solvent, and at least one other phase is an aqueous phase.

11. The emulsion according to claim 10, wherein the organic solvent is selected from the group consisting of hydrophilic organic solvents, lipophilic organic solvents, amphiphilic solvents and mixtures thereof.

12. The emulsion according to claim 10, wherein the organic solvent is isononyl isononanoate.

13. The emulsion according to claim 10, wherein the photochromic coloring agent is present in the fatty phase, and the non-photochromic coloring matter is present in the aqueous phase.

14. The emulsion according to claim 10, wherein the non-photochromic coloring matter is present in the fatty phase, and the photochromic coloring agent is present in the aqueous phase.

15. A composition comprising the emulsion according to claim 1 and at least one additive selected from the group consisting of preservatives, fatty phase thickeners, aqueous phase thickeners, perfumes, lipophilic active agents, hydrophilic active agents, antioxidants, colorants, essential oils, plant extracts, vitamins, derivatives of vitamins, sphingolipids, liposoluble polymers, and mixtures thereof.

16. The composition according to claim 15, wherein the additive is selected from the group consisting of polysaccharide biopolymers, synthetic polymers, hydrating agents, UVA filters, UVB filters, vitamin A, vitamin B, vitamin C, vitamin E, ccramides, polyhutenc, polyalkenes, polyacrylate, silicone polymers compatible with fatty bodies and mixtures thereof.

17. The emulsion according to claim 1, wherein the emulsion is in the form of a product for the care, treatment, or make-up of the skin and/or its appendages.

18. The emulsion according to claim 1, wherein the photochromic coloring agent is present in an amount of from 1 to 16% by weight of the total weight of the emulsion.

19. The emulsion according to claim 1, wherein the non-photochromic coloring matter is a pigment present in an amount of from 0.01 to 5% by weight of the total weight of the emulsion.

20. The emulsion according to claim 15, comprising a liposoluble polymer, wherein the liposoluble polymer is a hydrocarbon.

21. A method comprising applying a composition comprising the emulsion of claim 1 to the skin and/or appendages of the human face and/or human body.

22. A method comprising protecting the skin and/or appendages of the human face and/or human body by applying a composition comprising the emulsion of claim 1 to the skin.

23. A method comprising mixing the emulsion of claim 1 with one or more compositions to form an ointment for treating and/or protecting the skin and/or appendages of the human face and/or human body.

24. A cosmetic composition comprising the emulsion of claim 1, wherein the cosmetic composition is capable of adapting to the environment.

25. A method for cosmetically treating human skin consisting of applying a composition comprising the emulsion as claimed in claim 1 to human skin.

26. A method for preparing a cosmetic composition consisting of mixing the emulsion of claim 1 with one or more cosmetic compositions to form a colored dermatological composition.

27. The emulsion of claim 17, wherein the product is a lipstick, shimmer stick, solid foundation cream, liquid foundation cream, eyebrow pencil, eyeliner, mascara, eyeshadow, tinted care cream, untinted care cream or nail varnish.

28. An emulsion comprising at least two phases, wherein one of said phases contains at least one photochromic coloring agent and the second of said phases contains at least one non-photochromic coloring matter, and wherein the $\Delta E_{15}$ value of the emulsion is higher than the $\Delta E_{15}$ value of the same emulsion which differs only in that the photochromic coloring agent and the non-photochromic coloring matter are present in the same phase.

29. A method of preparing an emulsion comprising combining at least two phases, wherein one of said phases contains at least one photochromic coloring agent and the second of said phases contains at least one non-photochromic coloring matter, and wherein the $\Delta E_{15}$ value of the emulsion is higher than the $\Delta E_{15}$ value of the same emulsion which differs only in that the photochromic coloring agent and the non-photochromic coloring matter are present in the same phase.

30. The emulsion according to claim 1, wherein the non-photochromic coloring matter is a pigment.

31. The emulsion according to claim 1, wherein the non-photochromic coloring matter is a lipophilic colorant.

32. The emulsion according to claim 1, wherein the non-photochromic coloring matter is a hydrophilic colorant.

\* \* \* \* \*

UNITED STATES PATENT AND TRADEMARK OFFICE
CERTIFICATE OF CORRECTION

PATENT NO. : 7,776,316 B2
APPLICATION NO. : 10/168537
DATED : August 17, 2010
INVENTOR(S) : Richard Kolodziej et al.

It is certified that error appears in the above-identified patent and that said Letters Patent is hereby corrected as shown below:

Column 14, line 20, "ccramides, polyhutenc," should read --ceramides, polybutene,--.

Signed and Sealed this

Thirtieth Day of November, 2010

David J. Kappos
*Director of the United States Patent and Trademark Office*